United States Patent [19]

Olsen

[11] Patent Number: 5,055,100
[45] Date of Patent: Oct. 8, 1991

[54] SUCTION ATTACHMENT FOR ELECTROSURGICAL INSTRUMENTS OR THE LIKE

[76] Inventor: Eugene Olsen, 2100 Meredian Park Blvd., Concord, Calif. 94520

[21] Appl. No.: 367,841

[22] Filed: Jun. 19, 1989

[51] Int. Cl.$^5$ .............................................. A61B 17/20
[52] U.S. Cl. ....................................... 604/22; 604/19; 606/32; 606/37
[58] Field of Search .................... 128/752; 604/19-22; 606/32-42, 44, 49

[56] References Cited

U.S. PATENT DOCUMENTS

| | | | |
|---|---|---|---|
| 2,888,928 | 6/1952 | Seiger | 606/49 |
| 3,526,219 | 9/1970 | Balamuth | 128/752 |
| 3,825,004 | 7/1974 | Durden | 604/20 |
| 3,828,780 | 8/1974 | Morrison, Jr. | 606/20 |
| 4,299,221 | 11/1981 | Phillips et al. | 128/276 |
| 4,307,720 | 12/1981 | Weber, Jr. | 128/276 |
| 4,562,838 | 1/1986 | Walker | 128/303.14 |
| 4,644,951 | 2/1987 | Bays | 604/22 X |
| 4,747,820 | 5/1988 | Hornlein et al. | 604/22 |
| 4,815,642 | 3/1982 | Clark | 128/752 X |

FOREIGN PATENT DOCUMENTS 8604247 7/1986 PCT Int'l Appl. .................. 604/19

Primary Examiner—Robert A. Hafer
Assistant Examiner—Kerry Owens
Attorney, Agent, or Firm—Harris Zimmerman

[57] ABSTRACT

A clip-on attachment for a surgical instrument of the type having a handle which supports an electrode and switches for selectively applying high frequency electrical energy to the electrode acts to withdraw smoke, fumes or other fluids that may be produced in the region of of the electrode by contact with living tissue. The attachment includes an elongate tube which extends along the instrument handle and which preferably has a helically curved forward end that makes a partial turn around the forward end of the handle. A length of flexible tubing connecting with a source of low pressure is threaded through the tube to extend from the front end of the tube towards the electrode. Resilient clamps on the tube clasp the instrument handle while enabling axial sliding movement and partial rotation of the attachment around the instrument handle to enable repositioning of the flow intake under different operating conditions.

8 Claims, 2 Drawing Sheets

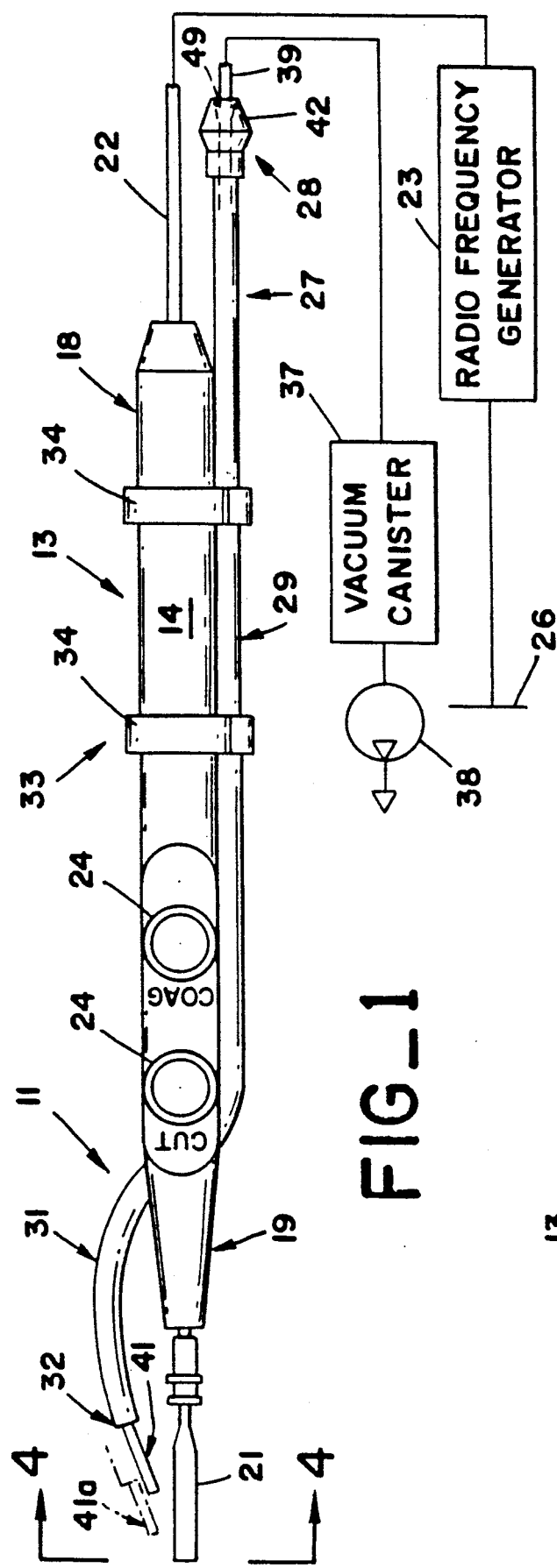
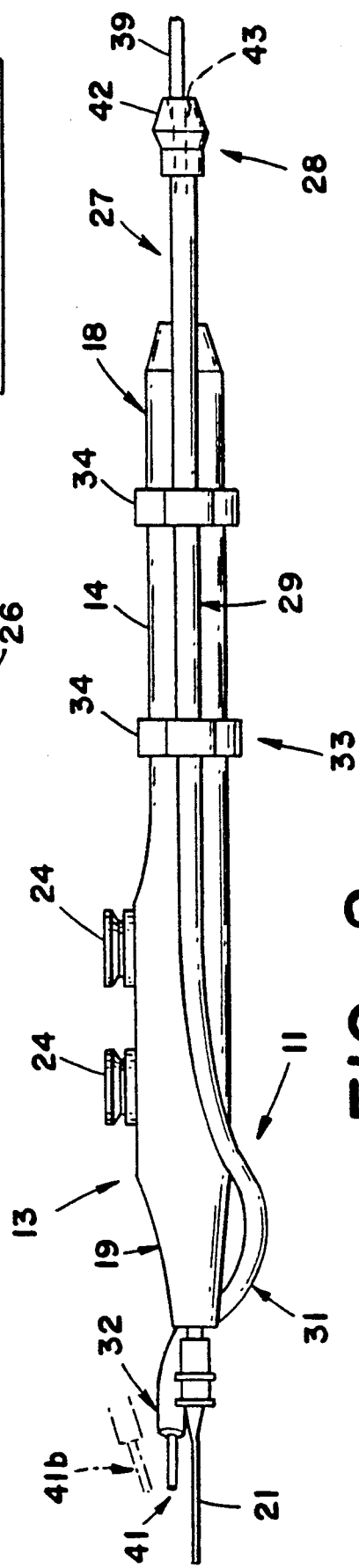

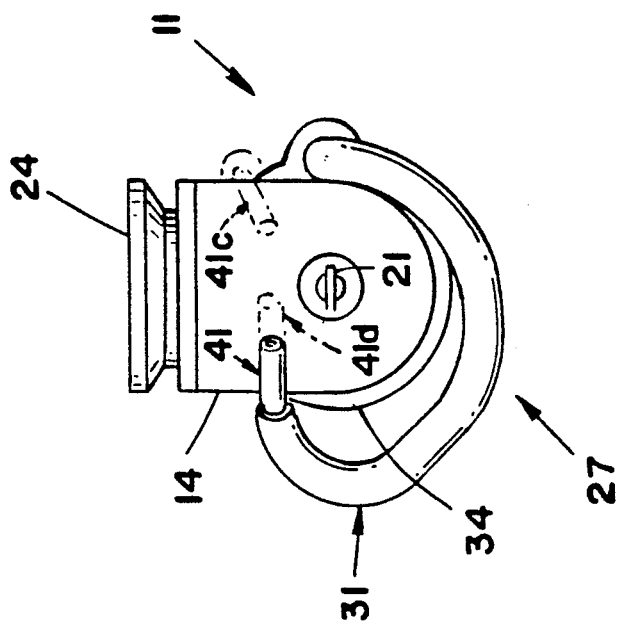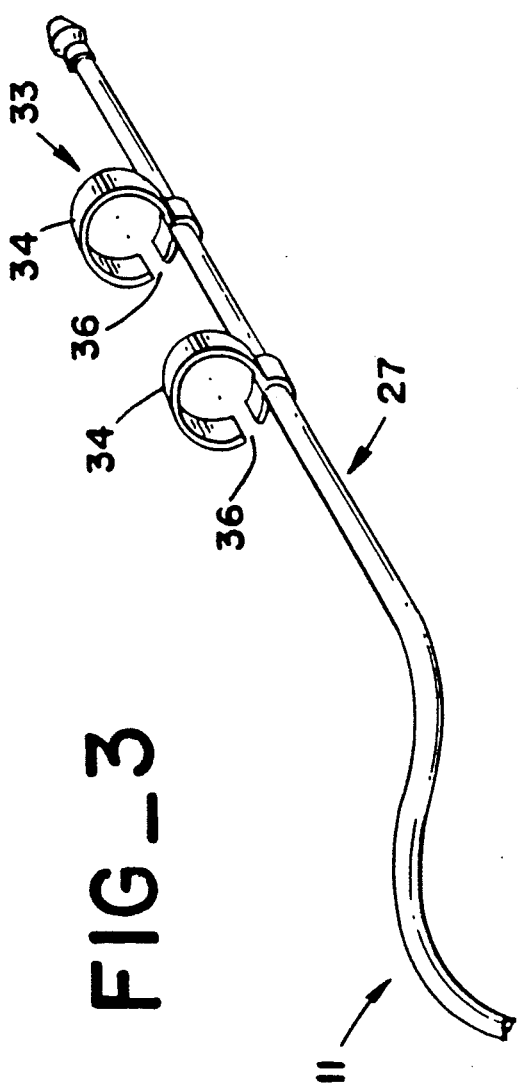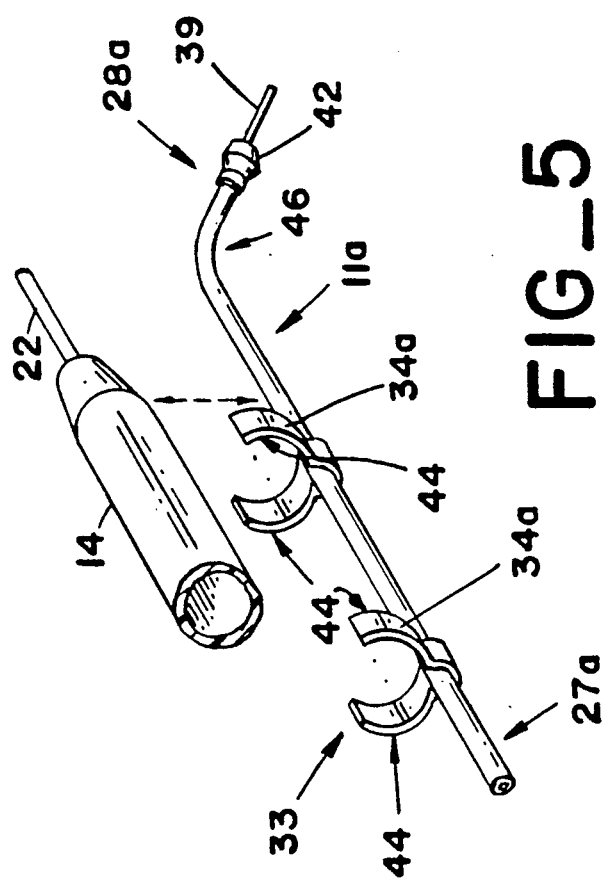

SUCTION ATTACHMENT FOR ELECTROSURGICAL INSTRUMENTS OR THE LIKE

TECHNICAL FIELD

This invention relates to surgical equipment and more particularly to apparatus for removing smoke, fumes or other fluids from the vicinity of the electrode of a handheld electrosurgical instrument or the like.

BACKGROUND OF THE INVENTION

A typical electrosurgical instrument includes a handle from which a small electrode extends, a cable extending from the handle to a source of high frequency electrical energy and one or more switches on the handle for selectively energizing the electrode. Contact of the energized electrode with living tissue results in concentrated localized heating enabling the instrument to be used for cutting, excising of unwanted tissue and coagulation of tissue to inhibit bleeding. Such instruments are well established as the preferred tool for many surgical procedures.

Use of an electrosurgical instrument typically causes a generation of smoke. This can obscure the surgeon's view of the tissue which is being operated on and can be disturbing to an un-anesthetized patient. Disagreeable odors may also be produced. Other fluids, such blood or applied saline solution, may also accumulate in the region where the electrode contacts the tissue.

Aspirating apparatus for removing such fluids from the operating site can greatly facilitate the surgeon's activities and provide a more comfortable environment for all persons who are present during use of an electrosurgical instrument.

Smoke and other fluids can be withdrawn from the vicinity of the electrode through a flexible tube which is connected to a vacuum canister. This complicates procedures and can be a distraction if the tube must be held and manipulated by the surgeon. It has been considered preferable to have another medical person operate the aspirator so that the surgeon may concentrate on the cutting or coagulation operations and have both hands available for necessary procedures. The need for additional personnel adversely affects the costs of electrosurgery.

Some prior electrosurgical instruments have been provided with a built-in internal passage connectable to a vacuum canister through tubing and which has one or more intake openings at the front end of the handle. Such instruments can avoid the need for additional personnel and enable more direct control of aspiration by the surgeon under some conditions but are not ideally suited for these purposes. The fluid intake opening is situated at the rear of the electrode which position is not always the most effective one for sucking in smoke or other fluids. A more forward intake location is preferable under many operating conditions. The optimum intake location is also influenced by variables such as the orientation in which the instrument is held, variable ambient air flows and the like. Built-in aspirators of the kind described above do not permit any adjustment to suit changing operating conditions.

Built-in aspirator ducts and fittings also increase the bulk and cost of manufacture of electrosurgical instruments. Current medical procedures favor the use, where possible, of low cost disposable instruments which can be discarded after a single use rather than instruments which must be sterilized for reuse.

The present invention is directed to overcoming one or more of the problems discussed above.

SUMMARY OF THE INVENTION

In one aspect, the present invention provides a suction attachment for a handheld electrosurgical instrument or the like which has a tubular handle with front and back ends and an electrode extending from the front end of the handle. The attachment includes a tube for disposition adjacent the handle and which has a back end adapted for connection to a source of low fluid pressure, an intermediate section proportioned to extend along the exterior surface of the handle and a front end shaped to extend into proximity with the electrode in spaced apart relationship with the electrode when the intermediate section extends along the handle surface. Clamping means provide for selectively clamping the intermediate section of the tube to the instrument handle.

In another aspect of the invention, the clamping means is adapted to frictionally grip the instrument handle while enabling rotation of the tube about the axis of the handle and sliding movement along the handle by application of sufficient force.

In another aspect, the invention provides a suction attachment for an electrosurgical instrument of the type having a tubular handle, an electrode extending from the front end of the handle and an electrical cable extending from the back end of the handle. The attachment includes a hollow tube having a back end adapted for connection to a source of low fluid pressure, an intermediate portion shaped for extension along the rearward region of the handle and a helically curved forward portion shaped to extend partially around the forward region of the handle and to situate the front end of the tube in the region of the electrode in spaced apart relationship with the front end of the electrode. At least one clamp member is secured to the intermediate portion of the tube and is shaped to clasp the rearward region of the handle to hold the attachment on the handle. The clamp member is formed of resilient material enabling the attachment to be rotationally turned relative to the handle and to be slid along the handle.

In still another aspect, the invention provides an electosurgical instrument Of the form having a tubular handle with an electrode extending from the forward end and switch means at a intermediate region of the handle for selectively applying radio frequency electrical energy to the electrode. A detachable suction attachment on the instrument includes a tube having a forward end situated in the region of the electrode, a helically curved forward portion which turns partially around the forward region of the handle in front of the switch means and a rearward portion which extends along the rearward region of the handle. A length of flexible tubing extends through the tube and has a fluid intake end which extends from the forward portion of the tube towards the electrode, the opposite end of the flexible tubing being connectable to a source of low fluid pressure. The tube is clamped to the handle by means which enable sliding movement of the tube along the handle and rotational movement of the tube around at least a portion of the circumference of the handle.

The invention provides an aspirating attachment which can be quickly and easily clipped onto an electrosurgical instrument or the like and which is highly effective for withdrawing smoke or other fluids from the vicinity of the tissue which is being operated on with the instrument. In the preferred form of the invention, the fluid intake of the attachment can be positioned at a selected location around the circumference of the electrode and can be advanced or retracted relative to the tip of the electrode. This enables more effective aspiration of fluids under different operating conditions and enables adjustments to avoid obscuring of the surgeon's view when the instrument is held in different orientations. Additional medical personnel are not needed for the purpose of removing smoke, fumes and the like from the vicinity of tissue being operated upon and the aspiration procedure is under the direct control of the surgeon.

BRIEF DESCRIPTION OF THE DRAWINGS

FIG. 1 is a top view of an electrosurgical instrument equipped with a suction attachment in accordance with the preferred embodiment of the invention, certain remote components to which the instrument and attachment are connected being shown in schematic form.

FIG. 2 is a side view of the electrosurgical instrument and attachment of FIG. 1.

FIG. 3 is a perspective view of the suction attachment of the preceding figures shown detached from the electrosurgical instrument.

FIG. 4 is a front view of the instrument and attachment taken along line 4—4 of FIG. 1.

FIG. 5 is a perspective view of the rear portion of another embodiment of the suction attachment.

DETAILED DESCRIPTION OF THE PREFERRED EMBODIMENTS

Referring to FIGS. 1 and 2 in conjunction, a suction attachment 11 in accordance with this embodiment of the invention is designed to clip on to an electrosurgical instrument 13 which may itself be of known construction and which will therefore be described only briefly to the extent necessary to understand the coaction of the attachment 11 with the instrument.

Such instruments 13 typically have a handle 14 with a tublular rear portion 18 and a tapered forward portion 19 from which a small blade-like electrode 21 extends. A flexible electrical cable 22 extends from the back of handle 14 to a source of high frequency electrical energy such as a radio frequency generator 23. Finger operated switch buttons 24 are present on an intermediate region of handle 14 to enable the surgeon to selectively apply the high frequency electrical energy to electrode 21. Two such switch buttons 24 are present as a relatively intense and continuous energization of electrode 21 is preferable for cutting operations while a pulsed energization of lesser intensity is preferred where coagulation alone is to be effected.

A continuous current path is established during use of the electrosurgical instrument by disposing another much larger electrode 26 against the patient's skin which electrode is connected to the other terminal of radio frequency generator 23. Contact of the instrument electrode 21 with the patient's tissue then closes the circuit. Tissue in the small region that is contacted by instrument electrode 21 is strongly heated to the point of cutting into the tissue if desired. Significant heating does not occur elsewhere in the patient's body nor at the broad return electrode 26. The current disperses throughout a much broader flow path at such locations and is therefore not concentrated enough at any specific point to cause a significant amount of heating.

Suction attachment 11 functions to remove the smoke and aromatic gases which may be produced by the intense heating of tissue at the point of contact with electrode 21. The attachment 11 includes an elongate hollow tube 27 which is clipped on the instrument handle 14 in a manner to be hereinafter described in more detail. The back end 28 of tube 27 is situated to the rear of handle 14 and an intermediate portion 29 of the tube is preferably linear and extends along the rear portion of the handle, in parallel relationship to the surface of the handle, to the region of the switch buttons 24. The forward portion 31 of tube 27 is shaped to situate the front end 32 of the tube in the vicinity of the electrode 21 in spaced apart relationship with the electrode. In the preferred form, the forward portion 31 of tube 27 has a helical curvature and is proportioned to extend around approximately 180 degrees of the circumference of the handle 14. This locates the front or intake end 32 of the tube 27 at the opposite side of the handle 14 from the more rearward portions 28, 29 of the tube and enables positioning of the intake end 32 directly above electrode 21, when desired, as will hereinafter be further described.

Clamping means 33 provide for selectively clamping the tube 27 to handle 14 in a manner which enables the attachment 11 to be slid longitudinally along the handle by application of sufficient force and which also enables the attachment to be turned for a limited distance about the axis of the handle.

In the preferred form, the clamping means 33 includes a pair of spaced apart ring shaped clamp members 34 formed of resilient material and being proportioned to encircle and clasp the handle 14 at locations situated behind switches 24. Referring to FIG. 3, clamp members 34 are discontinuous rings as each is interrupted by a small slot 36. In the relaxed state, clamp members 34 have an inside diameter slightly smaller than the outside diameter of handle 14. Referring jointly to FIGS. 1 and 3, slots 36 enable the resilient clamp members 34 to expand slightly as the back end of handle 14 is forced into the clamp members. The members 34 then frictionally grip handle 14 and secure attachment 11 to the instrument 13 while allowing longitudinal and/or rotational readjustment of the position of the attachment by application of sufficient force. Slots 36 also provide for entry of the electrical cable 22 into clamp members 34 prior to the time that the back end of handle 14 is forced into the clamp members.

The two clamp members 34 can, if desired, be replaced with a single relatively long clamp member of otherwise similar shape.

Referring to FIG. 1, suction is created by connection of attachment 11 to a source of low pressure such as a vacuum canister 37 which is maintained in a low pressure condition by a suction pump 38, the connection being made through a length of flexible tubing 39. Tubing 39 may, if desired, simply connect the back end 28 of tube 27 to canister 37 but it is preferred to use small tubing which can be inserted into the back end of tube 27 and be threaded through the tube until the front end 41 of the tubing extends a small distance forward from the front of tube 27. This further extends the range of available positional adjustments of the intake of the suction attachment as will hereinafter be further discussed. The outside diameter of tubing 39 preferably conforms closely with the internal diameter of tube 27 as frictional resistance then tends to immobilize the tubing within the tube except when a sizable force is deliberate applied to change the location of the front end 41 of the tubing relative to electrode 21.

Threading of the tubing 39 into tube 27 is facilitated by an enlargement 42 at the back end 28 of the tube which has a conical entryway 43 into the tube.

During operation, the inflow of air into the front end 41 of tubing 39 entraps smoke, fumes and other fluids that may be present in the vicinity of electrode 21 and carries such fluids to canister 37. The optimum location of the intake of the attachment 11 relative to electrode 21 may vary under different operating conditions. It is generally desirable the front end 41 of tubing 39 be at least slightly above the electrode so that it does not prevent desired contact of the electrode with the patient's tissue and since smoke and hot gases tend to rise from the region where they are being generated. It is frequently desirable that the front end 41 of tubing 39 be displaced slightly to one side of electrode 21 to avoid obscuring the surgeon's view of tissue which is being operated upon or, in some cases, because of the effect of ambient air currents on the path of the smoke or the like. A position to the right of electrode 21 is usually preferable to a right handed surgeon and a leftward displacement more suitable for a left handed surgeon unless the conformation of the patient's body in the region being operated and/or the orientation of the instrument 13 dictates a different positioning of the intake end 41.

The previously described several forms of possible adjustment of the attachment 11 on instrument 13 enable the intake 41 to repositioned as desired to accommodate to changing conditions such as those discussed above. Referring to FIG. 1, the attachment 11 may be slid forward of handle 14 to advance the intake 41 towards the tip of electrode 21 as depicted by dashed lines 41a or may be slid backward along the handle to locate the intake in a more rearward position. Referring to FIG. 2, the attachment 11 may be turned about the axis of handle 14 to raise intake 41 relative to the electrode 21 as depicted by dashed lines 41b or may be oppositely turned to lower the intake relative to the plane of the electrode. Referring to FIG. 4, the attachment can be further turned to bring intake 41 around to the opposite side of electrode 21 as depicted by dashed lines 41c. The range of available positions for the intake 41 is still further increased in that intake end 41 of tubing 39 may be advanced further out of tube 27 or pulled partially back into the tube as shown at 41d.

Tube 27 is preferably formed of a non-resilient, bendable material such as malleable metal or plastic or both. This enables still greater flexibility in the positioning and orientation of the suction inlet as the forward portion 31 of the tube 27 may be bent into any of various configurations as might be appropriate to the particular operation and the particular instrument 13.

Referring again to FIGS. 1 and 2, the above described embodiment of the attachment 11 is easily installed on the instrument 13 by a telescoping movement of the rear portion of handle 14 into the clamp members 34 as previously described which motion may need to be accompanied by a partial turning of the handle relative to the attachment to bring the protuberant switches 24 into the helically curved forward portion 31 of the attachment. The attachment 11 then cannot be dislodged by any sidewardly directed forces which might be exerted on tube 27. FIG. 5 depicts a modification of the clamping means 33a which enables the attachment 11a to be snapped on to handle 14 even more quickly although it is less resistant to dislodgement. In particular, the clamping members 34a of this embodiment have oppositely directed arcuate resilient arms 44 shaped to clasp the handle 14 and which jointly extend around just slightly more than 180 degrees of the circumference of the handle. Thus the handle 14 may be forced into the clamping members 34a by a sideward motion rather than the telescoping movement of the previously described embodiment.

The back end 28a of the tube 27a of the modification shown in FIG. 5 has an outwardly curved region 46 which situates the end enlargement 42 further away from electrical cable 22. This makes it easier to pull or push on tubing 39 to advance or retract it relative to tube 27a as previously described.

Referring again to FIGS. 1 and 2, the suction attachment 11 is usable for aspirating liquids such as blood or saline solution from the tissue which is being operated on as well as serving to suppress smoke and odors. The intake 41 can be temporarily advanced, if necessary, or otherwise repositioned to contact accumulations of such liquids without interference from the electrode 21.

While the invention has been described with respect to certain preferred embodiments for purpose of example, many variations and modifications of the construction are possible and it is not intended to limit the invention except as defined in the following claims.

I claim:

1. A suction attachment for use with a handheld electrosurgical instrument or the like and for use with a source of low fluid pressure that has flexible vacuum tubing extending therefrom which instrument has a tubular handle with front and back ends and an electrode extending from the front end of said handle, said suction attachment for use with said instrument and low fluid pressure source being comprised of:

a tube adapted to be clamped on to said instrument handle in an orientation at which said tube extends along at least a portion of said instrument handle between said front and back ends thereof, said tube having a back end adapted for receiving said flexible vacuum tubing, an intermediate section proportioned to extend along the exterior surface of said instrument handle and a front end shaped to extend apart relationship therewith when said suction attachment is clamped on to said instrument handle with said intermediate section of said tube being directed along said handle surface, and clamping means for selectively clamping said intermediate section of said tube to said instrument handle wherein said clamping means is adapted to frictionally grip said surface of said instrument handle while enabling turning of said suction attachment about the axis of said handle by application of sufficient torsional force to change the angular position of said front end of said tube relative to said axis and said electrode, and wherein said clamping means further enables sliding movement of said tube along said handle by application of sufficient axial force to change the longitudinal position of said front end of said tube relative to said electrode.

2. A suction attachment for use with a handheld electrosurgical instrument or the like and for use with a source of low fluid pressure that has flexible vacuum tubing extending therefrom which instrument has a tubular handle with front and back ends and an electrode extending from the front end of said handle, said suction attachment for use with said instrument and low fluid pressure source being comprised of:

a tube adapted to be clamped on to said instrument handle in an orientation at which said tube extends along at least a portion of said instrument handle between said front and back ends thereof, said tube having a back end adapted for receiving said flexible vacuum tubing, an intermediate section proportioned to extend along the exterior surface of said instrument handle and a front end shaped to extend into proximity to said electrode of said instrument in spaced apart relationship therewith when said suction attachment is clamped on to said instrument handle with said intermediate section of said tube being directed along said handle surface, and clamping means for selectively clamping said intermediate section of said tube to said instrument handle wherein said tube has a helically curved forward portion shaped to partially encircle the forward portion of said handle.

3. A suction attachment for use with a handheld electrosurgical instrument or the like and for use with a source of low fluid pressure that has flexible vacuum tubing extending therefrom which instrument has a tubular handle with front and back ends and an electrode extending from the front end of said handle, said suction attachment for use with said instrument and low fluid pressure source being comprised of:

a tube adapted to be clamped on to said instrument handle in an orientation at which said tube extends along at least a portion of said instrument handle between said front and back ends thereof, said tube having a back end adapted for receiving said flexible vacuum tubing, an intermediate section proportioned to extend along the exterior surface of said instrument handle and a front end shaped to extend into proximity to said electrode of said instrument in spaced apart relationship therewith when said suction attachment is clamped on to said instrument handle with said intermediate section of said tube being directed along said handle surface, and clamping means for selectively clamping said intermediate section of said tube to said instrument handle wherein said flexible tubing which extends from said source of low fluid pressure is threaded through said tube and has an end which extends from said front end of said tube towards said electrode when said suction attachment is clamped on to said instrument handle.

4. The apparatus of claim 3 wherein said tube has an internal passage through which said tubing extends, said passage being proportioned to frictionally grip said tubing while enabling longitudinal sliding movement of said tubing relative to said tube by application of sufficient force.

5. A suction attachment for use with a handheld electrosurgical instrument or the like and for use with a source of low fluid pressure that has flexible vacuum tubing extending therefrom which instrument has a tubular handle with front and back ends and an electrode extending from the front end of said handle, said suction attachment for use with said instrument and low fluid pressure source being comprised of:

a tube adapted to be clamped on to said instrument handle in an orientation at which said tube extends along at least a portion of said instrument handle between said front and back ends thereof, said tube having a back end adapted for receiving said flexible vacuum tubing, an intermediate section proportioned to extend along the exterior surface of said instrument handle and a front end shaped to extend into proximity to said electrode of said instrument in spaced apart relationship therewith when said suction attachment is clamped on to said instrument handle with said intermediate section of said tube being directed along said handle surface, and wherein at least said frontal end of said tube is formed of non-resilient bendable material, and clamping means for selectively clamping said intermediate section of said tube to said instrument handle.

6. A suction attachment for use with an electrosurgical instrument of the like and for use with a source of low fluid pressure that has flexible vacuum tubing extending therefrom which instrument has a tubular handle, an electrode extending from the front end thereof and an electrical cable extending from the back end thereof, said suction attachment for use with said instrument and low pressure fluid source being comprised of:

a hollow tube having an internal passage extending from the front end of the tube to the back end thereof, said tube having a back end adapted for receiving said flexible vacuum tubing, an intermediate portion shaped for extension along the rearward region of said instrument handle in substantially parallel relationship therewith, and a helically curved forward portion shaped to extend partially around the forward region of said instrument handle and to situate said front end of said tube in the region of said electrode in spaced apart relationship therewith when said suction attachment is attached to said instrument, and at least one clamp member secured to said intermediate portion of said tube and being shaped to clasp said rearward region of said instrument handle to hold said suction attachment thereon, said clamp member being formed of resilient material enabling said suction attachment to be rotated around a portion of the circumference of said instrument handle when said suction attachment is engaged thereon and to be slid along said handle by application of sufficient force.

7. The apparatus of claim 6 wherein said helically curved forward portion of said tube is proportioned to extend around substantially 180 degrees of the circumference of said forward region of said instrument handle when said suction attachment is clamped to said instrument.

8. In combination with an electrosurgical instrument of the form having a tubular handle with an electrode extending from the forward end thereof and switch means at an intermediate region of said handle for selectively applying radio frequency electrical energy to said electrode, a detachable suction attachment engaged on said handle, said detachable suction attachment being comprised of:

a tube having a forward end situated in the region of said electrode in spaced apart relationship therewith and having a helically curved forward portion which turns partially around the forward region of said handle in front of said switch means and a rearward portion which extends along the rearward region of said handle in substantially parallel relationship therewith, a length of flexible tubing extending through said tube and having a fluid intake end which extends from said forward portion of said tube towards said electrode and having an opposite end which is connectable to a source of low fluid pressure, and clamping means for clasping said tube on said handle while enabling sliding movement of said tube therealong and rotational movement of said tube around at least a portion of the circumference of said handle while said tube remains clasped on said handle.

* * * * *